(12) United States Patent
Kaliaperumal et al.

(10) Patent No.: US 10,945,957 B2
(45) Date of Patent: Mar. 16, 2021

(54) BIODEGRADABLE NANO-THERANOSTIC COMPOSITE AND PROCESS OF PREPARATION THEREOF

(71) Applicant: COUNCIL OF SCIENTIFIC & INDUSTRIAL RESEARCH, New Delhi (IN)

(72) Inventors: Selvaraj Kaliaperumal, Pune (IN); Rajendra Prasad, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/483,897

(22) PCT Filed: Feb. 9, 2018

(86) PCT No.: PCT/IN2018/050069
§ 371 (c)(1),
(2) Date: Aug. 6, 2019

(87) PCT Pub. No.: WO2018/146700
PCT Pub. Date: Aug. 16, 2018

(65) Prior Publication Data
US 2020/0237667 A1 Jul. 30, 2020

(30) Foreign Application Priority Data

Feb. 10, 2017 (IN) .............................. 201711004800

(51) Int. Cl.
| | | |
|---|---|---|
| A61K 9/127 | (2006.01) | |
| A61K 47/69 | (2017.01) | |
| A61K 47/02 | (2006.01) | |
| A61K 31/704 | (2006.01) | |
| A61K 31/7105 | (2006.01) | |
| A61K 31/711 | (2006.01) | |
| A61K 41/00 | (2020.01) | |
| B82Y 5/00 | (2011.01) | |

(52) U.S. Cl.
CPC ............ *A61K 9/1277* (2013.01); *A61K 47/02* (2013.01); *A61K 47/6911* (2017.08); *A61K 31/704* (2013.01); *A61K 31/711* (2013.01); *A61K 31/7105* (2013.01); *A61K 41/0052* (2013.01); *B82Y 5/00* (2013.01)

(58) Field of Classification Search
None
See application file for complete search history.

(56) References Cited

PUBLICATIONS

Po-Jung, et al., "Liposome/Graphene Oxide Interaction Studied by Isothermal Titration Calorimetry" Langmuir, 32(10):2458-2463 (2016).
Frost, et al., "Graphene Oxide and Lipid Membranes: Interactions and Nanocomposite Structures," Nano Letters, 12(7):3356-3362 (2012).
Zappacosta, et al., "Liposome-induced exfoliation of graphite to few-layer grapheme dispersion with antibacterial activity," Journal of Materials Chemistry B, 3(31):6520-6527 (2015).
Hu, et al., "Functionalized grapheme/C60 nanohybrid for targeting photothermally enhanced photodynamic therapy," RSC Advances, 5(1):654-664 (2015).
Sneider, et al., "Remotely Triggered Nano-Theranostic For Cancer Applications," Nanotheranostics, 1(1):1-22 (2017).
Folliet, et al., "Investigation of the Interface in Silica-Encapsulated Liposomes by Combining Solid State NMR and First Principles Calculations," J. Am. Chem. Soc., 133:16815-16827 (2011).
Kurapati, et al., "Near-infrared light-responsive grapheme oxide composite multilayer capsules: a novel round for remote controlled drug delivery," Chem. Comm., 49:734-736 (2013).

*Primary Examiner* — Brian J Davis
(74) *Attorney, Agent, or Firm* — Abelman, Frayne & Schwab; Stefan Knirr

(57) ABSTRACT

A biodegradable nano-theranostic composite comprising graphene oxide and lipid in the liposomes in the ration of 0.005 to 0.03 characterized in that the graphene oxide is coated as film on the liposome on the inner side and outer side of the liposome. The composite is capable of safely carrying sensitive cargo without premature release and is fluorescent and absorbs in the NIR region and can perform targeted combined chemo and photothermal therapy. The nanotheranostic nanocomposite is designed to collapse and biodegrade after use.

10 Claims, 6 Drawing Sheets

BIODEGRADABLE NANO-THERANOSTIC COMPOSITE AND PROCESS OF PREPARATION THEREOF

RELATED APPLICATIONS

This application is a national phase of International Application No. PCT/IN2018/050069 filed Feb. 9, 2018 and claims priority from Indian Patent Application No. 201711004800 filed Feb. 10, 2017, both incorporated by reference in their entirety.

FIELD OF THE INVENTION

The present invention relates to a biodegradable nano-theranostic composite useful in therapy and diagnostics and is capable of carrying cargo, biomolecules and dyes for avoiding premature release. Particularly, the present invention relates to a novel composite comprising graphene oxide and lipid in the liposomes in the ratio of 0.005 to 0.03 and a process for preparation and uses thereof. More particularly the present invention relates to a biodegradable nano-theranostic composite which is fluorescent and absorbs and emits in the NIR region and can perform targeted combined chemo and photothermal therapy.

BACKGROUND OF THE INVENTION

Fabricating a targeted multifunctional nanotheranostics can offer specific diagnosis and treatment of disease like cancer which is current demand for medical science. Various hybrids/composite nanoparticles have been explored for effectiveness of targeted therapies and organ safety for cancer treatment. However, each type of nanoformulation has its merits and limitations such as good therapeutic efficiency with poor dispersion and slow degradation. Although, many promising nano-composite have not yet qualified for their clinical application due to general concern about nonspecific targeting, biodegradation, long-term stability and poor imaging with low resolution. On the other hand, some soft nanohybrids (liposome-doxorubicin and paclitaxel-polymeric micelles, etc.) have been approved for clinical trials. Due to lack of ability to contrast in x-ray CT or to fluoresce in NIR imaging and hence a combined therapeutic modality with in a single system they are limited only for drug delivery. The specific targeting ability is a still major challenge for cancer theranostics. Recently, few nanocomposites (porphysome and conductive polymer, etc.) have been suggested for photothermal cancer therapy (PTT) but poor specific targeting ability became limitation for their clinical acceptance. Hence, designing/fabricating a biodegradable nanohybrid to integrate targeted imaging and localized cancer therapeutic modalities in a single system is a current demand. To achieve this, successful integration of various functions of different components inspite of inherent issues viz., slow degradation, non-specific targeting, poor dispersion, cytotoxicity and poor cellular intake are major concerns.

Article titled "Investigation of the Interface in Silica-Encapsulated Liposomes by Combining Solid State NMR and First Principles Calculations" by Nicolas Folliet et al. published in *Journal of the American Chemical Society*, 2011, 133, 16815-16827 reports the liposils synthesis follows a two-step process: first, the preparation of liposomes and then, the formation of a silica shell enclosing these liposomes. The liposomes were prepared according to the method described by Bangham. A suitable amount of L-α-dipalmitoylphosphatidylcholine, DPPC (phase transition temperature=41° C.) is dissolved in chloroform. After complete removal of the chloroform (at 40° C. under reduced pressure), phosphate buffer solution (PBS, 150 mM pH 7.4) is added to obtain a 10 mg 3 ml lipids suspension. This lipid suspension, containing large multilamellar vesicles, is then extruded above the transition temperature of the lipids (41° C.) using an extruder (Lipex biomembranes Inc.) with polycarbonate membrane (mean size diameter: 450, 200, and finally 100 nm, Nucleopore). Liposome size determination is performed by quasi-elastic light scattering at a 90° angle (SEMATECH, SM 633/RTG, France) using monomodal analysis. The mean size is determined to be ~100 nm.

Article titled "Remotely Triggered Nano-Theranostics For Cancer Applications" by Alexandra Sneider et al. published in *Nanotheranostics*, 1 Jan. 2017; 1(1): 1-22 reports the use of remotely triggered theranostic nanoparticles for cancer applications. Remote triggering mechanisms covered include photodynamic, photothermal, phototriggered chemotherapeutic release, ultrasound, electro-thermal, magneto-thermal, X-ray, and radiofrequency therapies. Some of the nanotheranostic platforms highlighted include photoactivatable multi-inhibitor nanoliposomes, plasmonic nanobubbles, reduced graphene oxide-iron oxide nanoparticles, photoswitching nanoparticles, multispectral optoacoustic tomography using indocyanine green, low temperature sensitive liposomes, and receptor-targeted iron oxide nanoparticles loaded with gemcitabine. Article titled "Near-infrared light-responsive graphene oxide composite multilayer capsules: a novel route for remote controlled drug delivery" by Rajendra Kurapati et al. published in *Chemical Communication*, 2013, 49, 734-736 reports a novel and simple route for near-infrared (NIR)-light controlled release of drugs has been demonstrated using graphene oxide (GO) composite microcapsules based on the unique optical properties of GO. Upon NIR-laser irradiation, the microcapsules were ruptured in a point-wise fashion due to local heating which in turn triggers the light-controlled release of the encapsulated anticancer drug doxorubicin (DOX) from these capsules.

There is literature wherein the individual GO component primarily plays plainly a role of diagnostic agent role. Photothermal response is an inherent property of GO. Nevertheless, GO as such is not good for cargo carrying. The cargo carrying capacity of GO is highly inferior (compared to that of liposome). Being 2D sheet, GO as such cannot encapsulate and protect any cargo for a safe delivery of sensitive cargo. Contrastingly, in our current invention GO plays multiple roles in addition. More than playing the usual role of diagnostic or photothermal, its judicious role here in our design is to fortify the liposomal wall that ensures (a) safe encapsulation of the cargo and (b) safe transport of sensitive cargo (c) exclusion of premature release. This unique capability and the special function was never designed or exploited before.

The individual components of the nanocomposite such as GO and liposomes are previously reported with its own popular inherent property and for applications based on them including the therapy and diagnostics. However, the very combination of these two are not known for theranostics. In specific each of the component is known to play a single known role. However, multiple role for each component is hardly realized and exploited. In contrast, the current invention involves a judicious design that resolves the inherent limitation of an individual component and uses the synergistic combination to unravel a totally unheard advantage.

Liposomes are known to be good cargo carriers due to their massive hydrophillic central cargo space however extremely unstable and highly sensitive to change in pH, ionic strength etc., hence are highly limited due to unresolved issue of premature release of cargo. The current invention while uses the advantage of liposome, resolves the stability issue by fortifying the highly fragile lipid membrane based liposomal wall with a tight enclosure of GO. The wall thus become highly stable even at pH as low as 5 or several hours and temperature as high as 50 degrees C. However, role of GO is not limited to this but extended to two more namely, to be a photothermal agent and also to fluoresce with red light. GO is not a good cargo carrier while it is composited with liposome, it can thus indirectly support the cargo carrying too. The judicious design, its successful synergism and the multifunctionality of the nanocomposite as demonstrated clearly with examples are invented and reported for the first time.

Integrating various modalities (NIR imaging and combined chemo-photothermal therapy) in a single system is interesting and thrust area for medical research. So far, synthesis of multifunctional nanohybrids for cancer theranostics have attempted but due to complicated synthesis, low aqueous solubility, slow degradation, poor contrast resolution for diagnosis, poor photothermal performance and nonspecific targeting, the attempted nanohybrids are far from in vivo testing or clinically acceptance.

There is need to provide solutions to all the above issues in addition to fulfilling many basic requirements for an ideal theranostics to a reasonable level that encourages further commercial viability.

OBJECTIVES OF THE INVENTION

The main objective of the present invention is to provide a nano-theranostic composite that is multifunctional and especially biodegradable for targeted therapy and diagnostics.

Another objective of the present invention is to provide a biodegradable NIR responsive red emissive composite for better diagnostics.

Still another objective of the present invention is to provide a nano-theranostic biodegradable composite wherein the composite is capable of carrying large cargo (drug/dye etc.)

Yet another objective of the present invention is to provide a nano-theranostic biodegradable composite wherein the composite is NIR responsive for high photothermal response.

Still yet another objective of the present invention is to provide a nano-theranostic biodegradable composite wherein the composite has a high targeting efficacy for site specific therapy.

Still yet another objective of the present invention is to provide a nano-theranostic biodegradable composite wherein the composite is biocompatible and safe for in vitro and in vivo trials.

Still yet another objective of the present invention is to provide a nano-theranostic biodegradable composite wherein the composite has a high viability of normal cells and collapses after accomplishing its designed mission and degrades.

SUMMARY OF THE INVENTION

Accordingly, the present invention provides nano composite comprising graphene oxide and lipid in liposomes in the ratio of 0.005 to 0.03, characterized in that the graphene oxide is coated as film on the liposome, said composite is optionally functionalized, wherein the said composite is useful for therapy and diagnostics and is biodegradable.

In an embodiment of the present invention, the said composite is fluorescent and absorbs in the Near-infrared region.

In another embodiment, the present invention provides a composition comprising the nano composite, along with a cargo selected from a drug, a biomolecule or a dye useful in therapy and diagnostics.

In still another embodiment of the present invention, the drug in the cargo is Doxorubicin and the biomolecule is Deoxyribonucleic acid or Ribonucleic acid.

In another embodiment, the present invention provides a process for the synthesis of the composite as claimed in claim 1, wherein said process comprises the steps of:
a) dissolving amphiphilic compounds or lipids in a volatile solvent to obtain a mixture;
b) removing of solvent from the mixture as obtained in step a), followed by adding phosphate-buffered saline containing fluorescent graphene oxide nanoflakes in the range of 0.5 to 3 mg, to obtain a lipid suspension in the form of multilamellar vesicles during film hydration process and
c) extruding the suspension of multilamellar vesicles as obtained in step (b) at the transition temperature in range of 40 to 50° C. of the lipids using an extruder with polycarbonate membranes to form said biodegradable Near-infrared responsive red emissive graphene oxide liposome nano-theranostic composite In yet another embodiment of present invention, the amphiphilic compounds or lipids are selected from L-alpha-dipalmitoylphosphatidylcholine, 1,2-Dimyristoyl-sn-glycero-3-phosphorylcholine and 1,2-Dimyristoyl-sn-glycero-3-phosphorylglycerol sodium salt.

In still another embodiment of present invention, the volatile solvent of step (a) is selected from chloroform, alcohol or mixtures thereof.

In still another embodiment, the present invention provides a process for synthesis of Graphene oxide nanoflakes comprising the steps of:
i). adding graphene oxide into concentrated solution of sulfuric acid and nitric acid at volume ratio of 3.3 to 2.8 followed by stirring for the time period in the range of 12 to 14 h at the temperature in the range of 35 to 40° C. to afford product and
ii). dialyzing the product of step i) between the temperature in the range of 35-40° C. of by dialysis bag (molecular weight cut-off 2000 Da) for a period in the range of 2 to 4 days to afford graphene oxide nanoflakes with specific emissions in the range of 600 to 850 nm.

In still another embodiment, the present invention provides a process for functionalization of the composite of claim 1 with a targeting ligand comprising the steps of:
i. activating the functional groups of graphene oxide nanoflakes present on the external surface of the composite by 1-Ethyl-3-(3-dimethylaminopropyl) carbodiimide/N-Hydroxysuccinimide agents followed by adding cystamine in the reaction mixture;
ii. anchoring the folic acid on the amine functionalized nanocomposite;
iii. mixing the aqueous solution of amine functionalized nanocomposite with activated folic acid and allowing reacting for 12 hours and iv. dialyzing the step iii mixture using dialysis bag (molecular weight cut-off 2000 Da) for a period in the range of 6 to 48 hours.

In still another embodiment of the present invention, the said process is carried out at the temperature in the range of 37° C. to 40° C.

ABBREVIATIONS

GOF: Graphene Oxide nanoFlakes
NIR: Near-infrared
DOX: Doxorubicin hydrochloride
TEM: Transmission Electron Microscopy
DPPC: L-alpha-dipalmitoylphosphatidylcholine
PBS: Phosphate Buffered Saline
EDAX: Energy Dispersive X-ray Microanalysis
EDC/NHS: 1-Ethyl-3-(3-dimethylaminopropyl) carbodiimide/N-Hydroxysuccinimide
SBF: Simulated Body Fluid

DETAILED DESCRIPTION OF THE INVENTION

The invention will now be described in detail in connection with certain preferred and optional embodiments, so that various aspects thereof may be more fully understood and appreciated.

In view of above, the present invention provides a nano-theranostic biodegradable composite comprising graphene oxide and lipid in the liposomes in the ration of 0.005 to 0.03 characterized in that the graphene oxide is coated as film on the liposome on the inner side and outer side of the liposome.

In a preferred embodiment, the composite is fluorescent and absorbs in the NIR region and can perform targeted combined chemo and photothermal therapy.

In another preferred embodiment, the composite is biodegradable NIR responsive for high photothermal response and applicable for better diagnostics.

The composite is capable of carrying cargo, wherein said cargo is selected from drug preferably Doxorubicin (DOX), biomolecules preferably RNA, DNA and like, dye etc.

The nano-theranostic biodegradable composite has high targeting efficacy for site specific therapy and high cell viability.

The nano-theranostic biodegradable composite is biocompatible and safe for in vitro and in vivo trials.

In an embodiment, the present invention provides a process for synthesis of red fluorescent graphene oxide nanoflakes (GOF) comprising the steps of:
 a) adding graphene oxide into concentrated solution of $H_2SO_4$ and $HNO_3$ at volume ratio of 3.3 to 2.8 followed by stirring for the time period ranging from 12 to 14 h at the temperature ranging from 35 to 40° C. to afford product;
 b) dialyzing the product of step (a) between the temperature range of 35-40° C. of by dialysis bag (molecular weight cut-off 2000 Da) for 2 to 4 days to afford graphene oxide nanoflakes (GOF) with specific emissions in the range of 600 to 850 nm.

Yet in another embodiment the present invention provides a process of synthesis of graphene oxide (GO), or reduced graphene oxide (rGO) or graphene, doped or undoped graphene, or chemically functionalized/physically modified graphene of any size.

Figure 1:
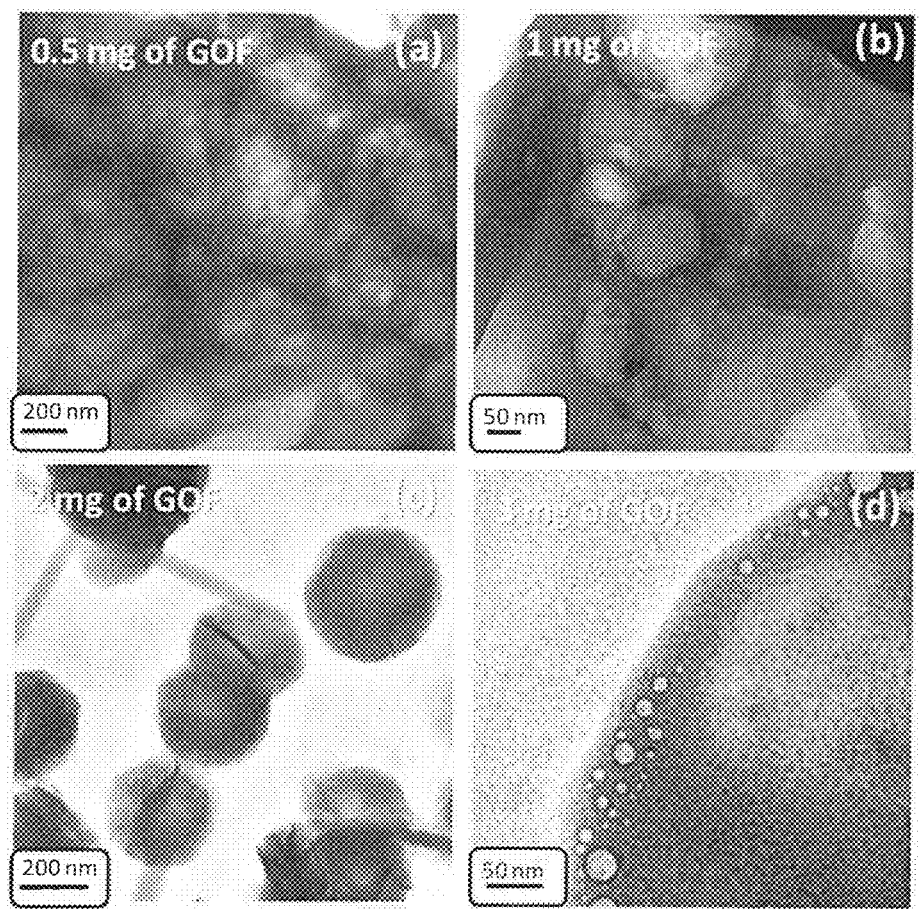
FIG. 1: TEM images of GOF supported Liposome nanaocomposite show the effect of GOF concentration on nanocomposite formation a) 0.5 mg of GOF b) 1 mg of GOF c) 2 mg of GOF d) 3 mg of GOF.

FIG. 1 depicts the optimization of the concentration of GOF to design the perfect GOF-liposome nanocomposite (TEM images). From FIG. 1 it is clear that lower concentration of GOF (0.5 and 1 mg) is not enough to cover the liposome fully whereas higher GOF concentration (3 mg) is disturbing the lipid self-assembly for liposome formation and also depicts the perfect size and shape maintained nanocomposites at moderate concentration of GOF (2 mg) where each liposome is fully covered/supported by GOF (FIG. 1 c). FIG. 1a showing un-matured nanocomposite which disintegrate during TEM imaging due electron exposure and lower support of GOF over liposome, FIG. 1b in red box free GOF can be seen and in yellow box pre-matured GOF supported liposome, in 1c a perfect GOF supported liposome where liposomes are fully covered with GOF and FIG. 1d in red box free GOF can be seen and in yellow box GOF supported liposome.

In another embodiment, the present invention provides a process for synthesis of small unilamellar vesicles (Liposomes) comprising the steps oft
 a) dissolving amphiphilic compounds or lipids that contains a head group and aliphatic long chains as observed in lipid in volatile solvent;
 b) removing completely volatile solvent to form to phospholipid film sample;
 c) adding PBS to phospholipid film of step (b) to obtain a lipid suspension in the form of large multilamellar vesicles during film hydration process;
 d) extrusion of suspension of multilamellar vesicles of step (c) above the transition temperature (41 to 43° C.) of the lipids using an extruder with polycarbonate membranes to form unilamellar Liposomes of diameter ranging from 30 nm to 10 micron.

In preferred embodiment, said amphiphilic compounds or lipids of step (a) are selected from amphiphilic or lipids molecules that is capable of making a liposome, preferably selected from L-alpha-dipalmitoylphosphatidylcholine (DPPC), 1,2-Dimyristoyl-sn-glycero-3-phosphorylcholine (DMPC), 1,2-Dimyristoyl-sn-glycero-3-phosphorylglycerol sodium salt (DMPG).

The volatile solvent of step (a) is selected from chloroform or other solvents such as alcohol in combination with chloroform.

Still in another embodiment, the present invention provides a process of fabrication of biodegradable NIR responsive red emissive graphene oxide liposome nano-composite comprising the steps of:
a) dissolving amphiphilic compounds or lipids in volatile solvent;
b) removing of solvent followed by adding PBS containing 0.5 to 3 mg of fluorescent GOF to obtain a lipid suspension in the form of the large multilamellar vesicles during film hydration process and
c) extruding the suspension of multilamellar vesicles of step (b) at the transition temperature range of 40 to 50° C. of the lipids using an extruder with polycarbonate membranes to form biodegradable NIR responsive red emissive graphene oxide liposome nano-composite.

In preferred embodiment, said amphiphilic compounds or lipids of step (a) are selected from amphiphilic or lipids molecules that is capable of making a liposome, preferably selected from L-alpha-dipalmitoylphosphatidylcholine (DPPC), 1,2-Dimyristoyl-sn-glycero-3-phosphorylcholine (DMPC), 1,2-Dimyristoyl-sn-glycero-3-phosphorylglycerol sodium salt (DMPG).

The volatile solvent of step (a) is selected from chloroform or other solvents such as alcohol in combination with chloroform.

Engineering of the biodegradable NIR responsive red emissive graphene oxide liposome nano-composite can be done by following above (a) to (c) steps and continuing the procedure by following drug loading experiment by using doxorubicin drug for filling hydrophilic cavity of liposome and calculating the mass of drug loaded into nanocomposite by subtracting the mass of drug in the supernatant from the total mass of drug in initial solution.

The volatile solvent is selected from chloroform or other solvents such as alcohol in combination with chloroform.

Yet in another embodiment, the present invention provides functionalization of biodegradable NIR responsive red emissive graphene oxide liposome nano-composite or nanocomposite with targeting ligand comprising the steps of:
a) activating the functional groups of GOF by EDC/NHS agents followed by adding cystamine in the reaction mixture;
b) anchoring the folic acid on the amine functionalized nanocomposite;
c) mixing the aqueous solution of amine functionalized nanocomposite with activated folic acid and allowing reacting for 12 hours;
d) dialyzing the step c mixture using dialysis bag (molecular weight cut-off 2000 Da) for 6 to 48 hours.

In preferred embodiment, said reaction is carried out at the temperature ranging from 37° C. to 40° C.

The present invention provides Scheme for nanocomposite fabrication as follow:
1) Multiple components are integrated for engineering a novel biodegradable NIR active red emissive GO flakes (GOF) supported liposome (FIG. 6)
2) First NIR active and red fluorescent GO flakes are prepared from graphene oxide (GO) via chemical cutting process at room temperature (37° C.).
3) Fluorescent GO flakes are mixed in lipid suspension and kept for film hydration.
4) Further, extrusion procedure is done to make the final product.
5) For specific targeting the designed nanocomposite is functionalized with folic acid as a targeting ligand.
6) Prior to cancer theranostics applications the designed nanocomposite is characterized using various techniques.

Figure 2:
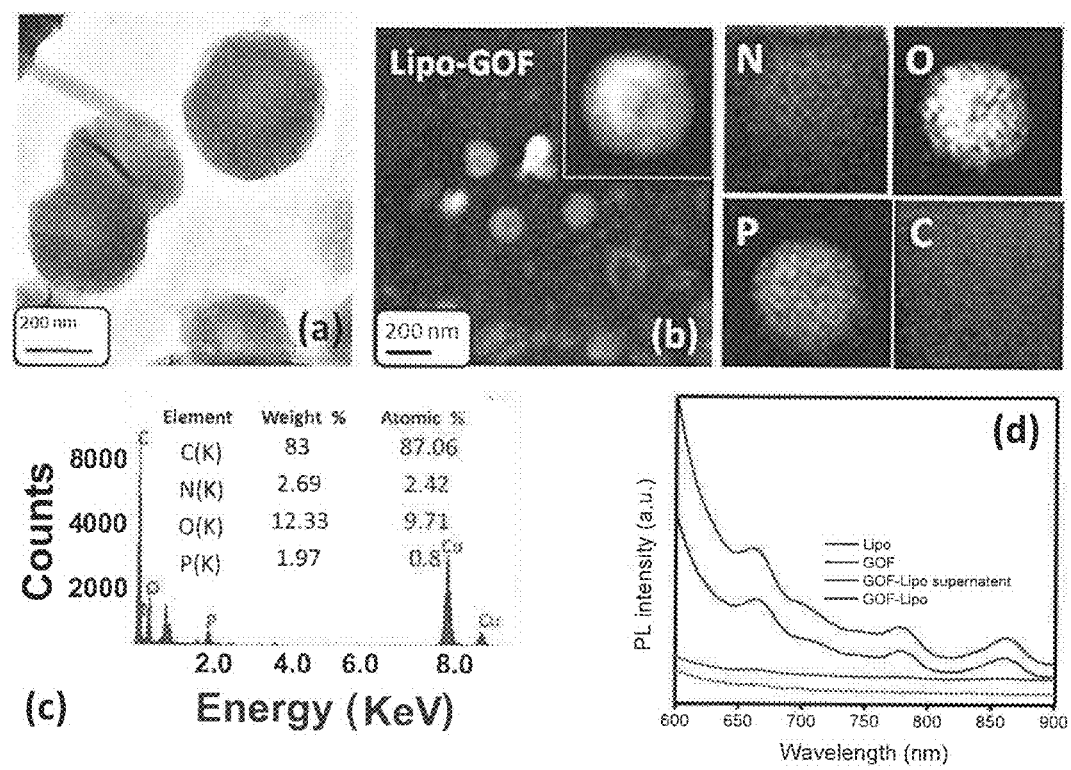
FIG. 2: (a) TEM image of GOF supported Liposome (b) elemental mapping of GO flakes supported liposome (c) EDAX elemental analysis (d) photo luminance spectra of liposome, GO flakes, GO flakes supported liposome.

FIG. 2 a depicts TEM image, it shows the spherical morphology of nanocomposite (~200 nm in size,). FIG. 2b depicts the multiple components of nanocomposite is confirmed through elemental mapping. FIG. 2c depicts EDAX analysis which shows the presence of all possible elements in nanocomposite. FIG. 2d depicts the NIR fluorescence (in the range of 600-950 nm) is confirmed by photoluminance spectra indicating excellent property for tumor or tissue monitoring during imaging and treatment.

Figure 3:
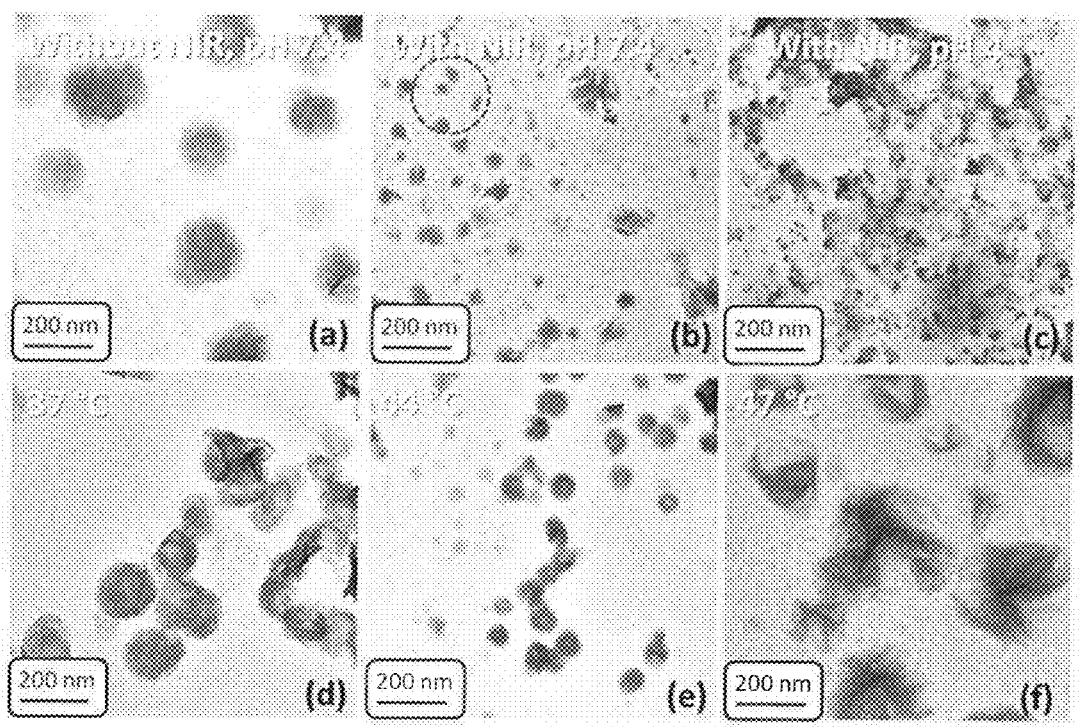
FIG. 3: TEM images reveal the degradation of nanocomposite in various conditions (a) neutral pH and at room temperature, (b) effect of NIR light. (c) effect of NIR and acidic pH and (d-f) effect of temperature (37 to 47° C.).

FIG. 3 shows TEM images reveal the degradation of nanocomposite in various conditions (pH, temperature and effect of NIR light) is understood through microscopic analysis and drug release kinetics. From microscopic analysis it is observed that the disintegration of nanocomposite after NIR laser treatment, acidic pH (4) and higher temperature (47° C.). Whereas, nanocomposite maintained its size and shape at physiological conditions (neutral pH, 7.4 and room temperature, 37° C.) which is due to favorable condition for DPPC liposome stability (phase transition temperature=41° C.). Further, the GOF-Liposome nanocomposite maintained its size and shape even beyond hyperthermia temperature (43° C.) and phase transition temperature treatment (44° C.). Stability of nanocomposite at higher temperature indicates the successful support of GOF for liposome.

Still yet in another embodiment, the present invention provides drug release study preferably for Doxorubicinhydrochloride (DOX).

FIG. 4a depicts the synthesized nanocomposite shows good dispersion ability in various media (PBS, saline and SBF). FIG. 4b depicts the photothermal performance of nanocomposite at various concentrations which reveals that designed system is capable of exhibiting hyperthermia (43° C.) within 2 min. by using 808 nm NIR laser source with low power density as less as 1 W. FIG. 4b shows photothermal performance of nanocomposite at various concentration black line for 0.2 mg, red for 0.5 mg, blue line for 1 mg and green line for 2.5 mg/mL. FIG. 4c depicts the triggered drug release response under NIR light exposure. FIG. 4c shows negligible drug release (~1%) is observed in neutral environment whereas maximum release (more than 40%) is observed in cancer mimicked environment and presence of NIR light. NIR responsive triggered drug release kinetics, black curve is for neutral pH (7.4), red is for effect of NIR in neutral pH, blue curve for acidic pH (4), green curve for effect of NIR in acidic pH.

Figure 4:
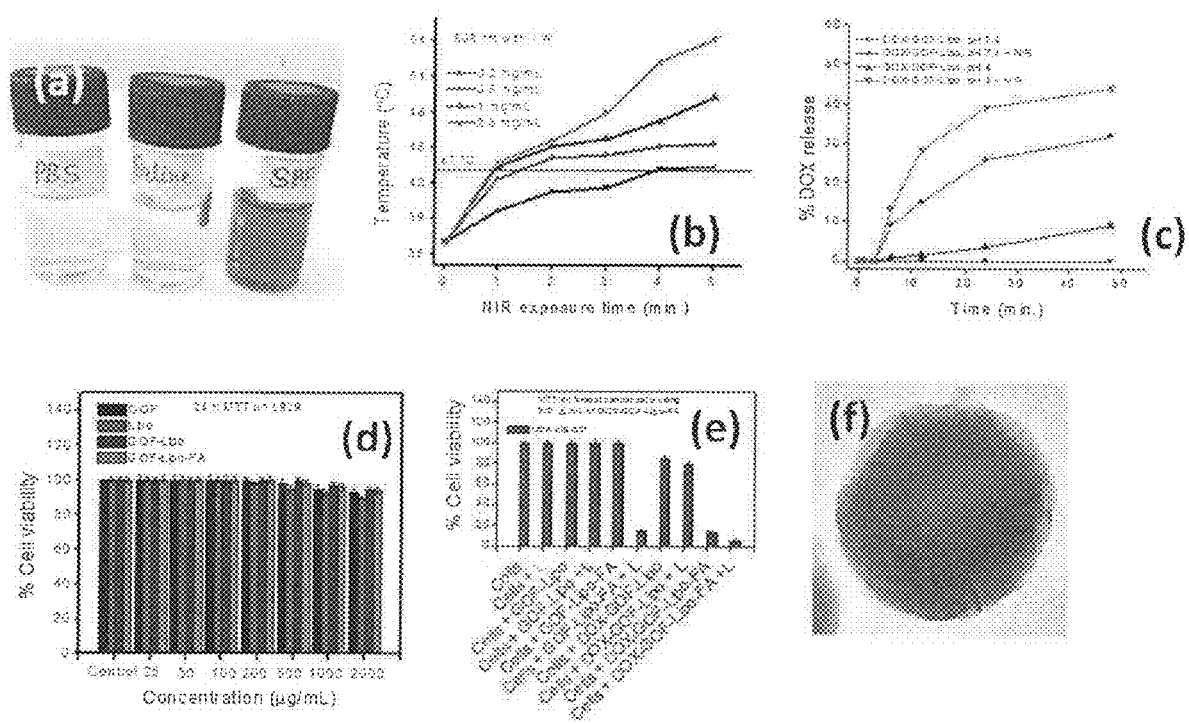
FIG. 4: (a) Dispersion test in various media such as PBS, saline and SBF, (b) Photothermal performance of nanocomposite at various concentration, (c) NIR responsive triggered drug release kinetics, (d) % cell viability of GOF, Lipo, and GOF-Lipo and GOF-Lipo-FA nanocomposites with normal L929 cell lines, (e) in vitro targeted cancer therapies and (f) microscopic image of single nanocomposite sphere.

FIG. 4 d shows good biocompatibility (more than 90%) of nanocomposite even at maximum concentration (2000 μg/mL). FIG. 4d shows % cell viability of GOF (black color), Lipo (red color), and GOF-Lipo (blue color) and GOF-Lipo-FA (green) nanocomposites with normal L929 cell lines. FIG. 4e shows targeted vitro therapeutic effects on breast cancer cell lines (MDA-MB-23). It is observed that only NIR laser, GOF-Lipo nanocomposite and NIR exposed GOF-Lipo nanocomposite before DOX loading and FA functionalization does not affect the cell death of MDA-MB-231 (cell viability is calculated more than 95%). In case of targeted photothermal therapy (treatment with GOF-Lipo-FA), the cell viability is calculated less than 20% while more than 95% cell viability is calculated before NIR treatment. The cell death is observed due to photothermal activity of nanocomposite (produced heat from GOF after NIR exposure) under NIR light exposure.

FIG. 4 e shows groups of treatment for individual targeted chemotherapy and synergistic combined chemo-photothermal therapy are also made; Group-1: for control, only breast cancer cells with and without NIR light (808 nm) exposure for 5 min., Group-2: GOF-Lipo and DOX@ GOF-Lipo treated cancer cells with and without 5 min. NIR exposure, Group-3: GOF-Lipo-FA and DOX@GOF-Lipo-FA treated cancer cells with and without 5 min. NIR exposure. Each set of treatment is tested through MTT assay and following cell viability is calculated.

For control, the viability is calculated 100% before and after NIR treatment which indicates that NIR does not affect the cells. GOF-Lipo shows 100% viability and DOX@ GOF-Lipo shows more than 90% (before NIR) and 85% cell viability (after NIR exposure, control). When cancer cell lines are treated with DOX loaded GOF-Lipo-FA the cell viability is calculated 15% before NIR exposure which indicates the chemotherapeutic effect on cancer cell lines. Further, in case of NIR light exposure, only 3% cell viability is calculated which is due to the effect of drug and heat produced by nanocomposited under NIR exposure (FIG. 4 e).

Still yet in another embodiment, the present invention provides in vitro studies by using L929 cells and MDA-MB-231 cancer cells.

Figure 5:
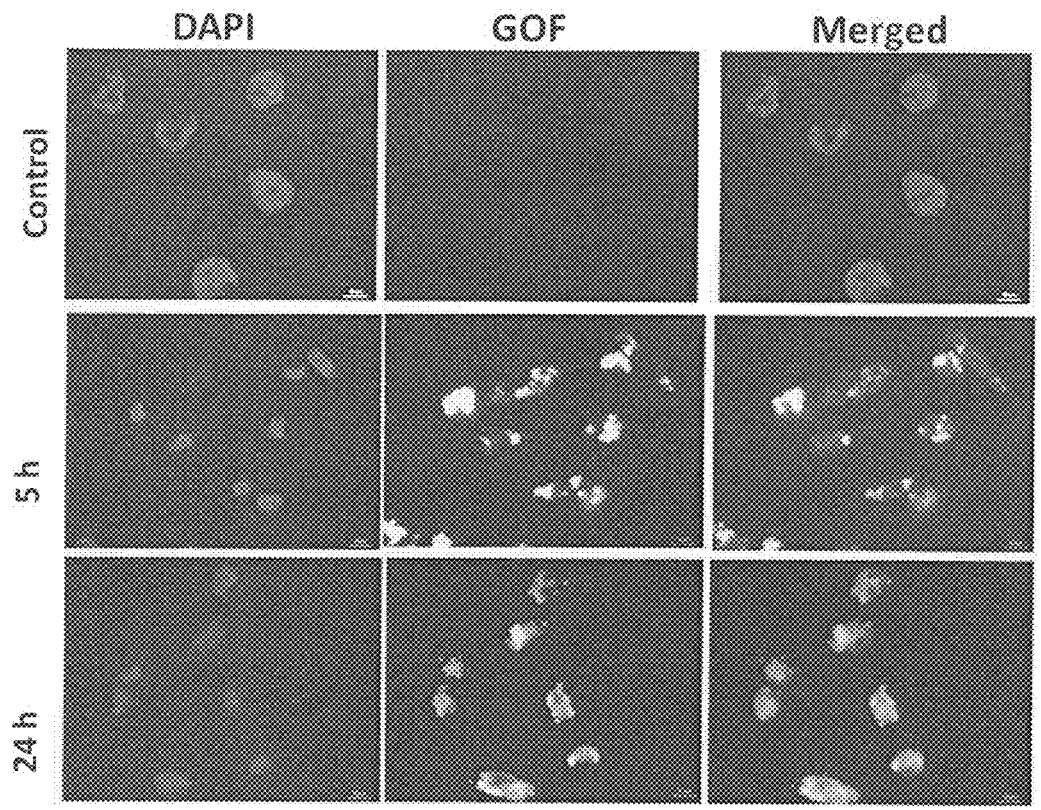
FIG. 5: Time dependent in vitro targeting ability and intracellular localization of nanocomposite for breast cancer cells (MDA-MB-231).

FIG. 5 shows time dependent in vitro targeting ability and intracellular localization of nanocomposite for breast cancer cells (MDA-MB-231), Blue color for DAPI which stain cell nuclei, red color for presence of GOF in cell interior. In addition, both blue and red color is seen in merged images. Time dependent cellular uptake and intracellular localization is observed through fluorescence microscopic image which indicates the multiple targeting ability of cell interior (cytoplasm and nuclei) by nanocomposite.

Figure 6:
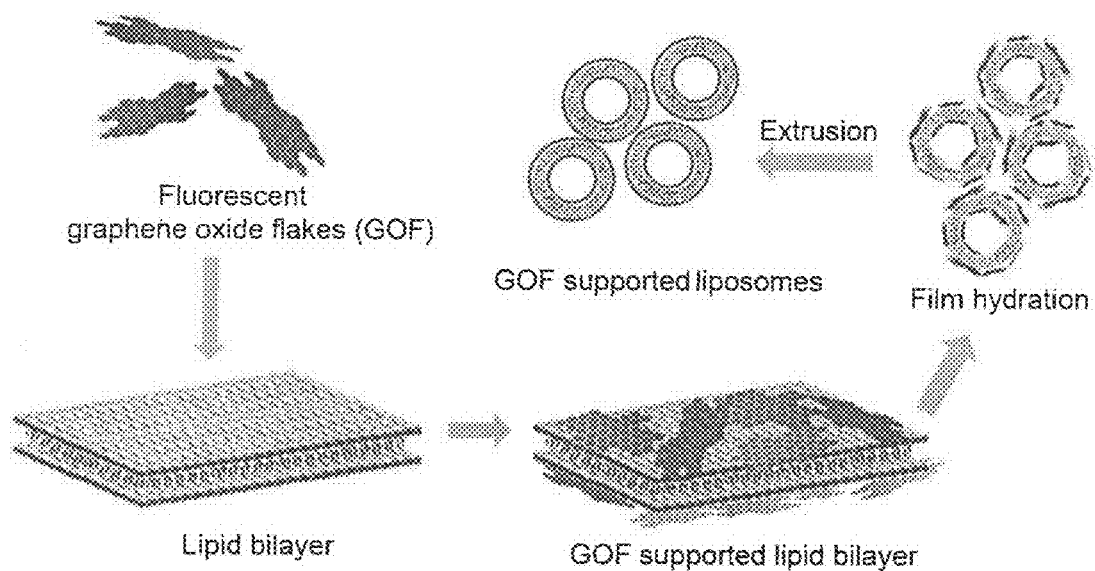
FIG. 6: Schematic of nanocomposite fabrication.

FIG. 6 depicts the designed nanocomposite where graphene oxide flakes are supported over liposome. The designed nanocomposite can be perform multiple tasks during fluorescent based diagnosis and medical treatment such as bio-imaging, chemotherapy and combined chemo-photothermal therapy.

Based on the above, the present invention effectively solves the problems and drawbacks in the prior art, and thus it fits the demands of the medical industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

EXAMPLES

Following examples are given by way of illustration therefore should not be construed to limit the scope of the invention.

Example 1: Materials and Characterization Techniques

L-alpha-dipalmitoylphosphatidylcholine, DPPC is ordered from Lipoid (Switzerland), Graphite powder, 1-ethyl-3-(3-dimethylaminopropyl) carbodiimide (EDC), N-hydroxysuccinimide (NHS), folic acid (FA), cystamine dihydrochloride, citric acid and 3-(4, 5-dimethylthiazol-2-yl)-2, 5-diphenyltetrazolium bromide (MTT) are purchased from Sigma-Aldrich Pvt. Ltd., USA. Sulphuric acid (98.08% $H_2SO_4$) and nitric acid (70% $HNO_3$) are purchased from Merck limited, Mumbai, India. Sodium carbonate ($Na_2CO_3$, 99.9%) is purchased from Fischer Scientific limited Mumbai. India. Dulbecco's modified Eagle's medium (DMEM), fetal bovine serum (FBS), phosphate-buffered saline (PBS), antibiotic-antimycotic solution and anticancer drug doxorubicin hydrochloride are procured from HiMedia Laboratories Pvt. Ltd., India. Milli-Q grade water ((Millipore)>18.2 MΩ cm) is used for all experiments. Synthesized nanocomposite is systematically characterized with various physicochemical techniques. The size and morphology of nanostructures are examined by transmission electron microscopy (TEM FE1 Tecnai T-20) operating at 200 kV and scanning electron microscopy (SEM). Samples for TEM are prepared by evaporating a droplet of sample onto 200 mesh carbon coated copper grid. Optical properties of nanocomposite are characterized by UV/visible/NIR (Jasco V570) and photoluminescence (Scinco, Korea) spectrophotometer using standard quartz cuvette having a path length of 1 cm. A Zetasizer ZS 90 apparatus utilizing 633 nm red laser (at 90° angle) from Malvern instruments is used for DLS measurements. Fourier transform infrared (FT-IR) spectra are recorded by using Perkin-Elmer FT-IR spectrum GX instrument. KBr crystals are used as the matrix for preparing samples. Digital photographs are captured in UV cabinet. AFM images are obtained from atomic force microscope (PSIA XE-100) on tapping mode. The samples for AFM measurements are prepared by drop casting on clean silicon wafers surface after ultrasonic treatment (Equitron ultrasonic cleaner). Bio-imaging and intracellular localization of drug and carrier is performed with the help of fluorescence microscope. The fluorescence microscopic images are taken by Carl Zeiss inverted fluorescence microscope model AXIO OBSERVER.Z1 using DAPI (350-430 nm blue) and rhodamine (480-580 nm red) filters.

Example 2: Engineering of Biodegradable Nanotheranostics a. Synthesis of Red Fluorescent Graphene Oxide Nanoflakes (GOF)

In a round bottom flask, 300 mg of graphene oxide is added into concentrated solution of $H_2SO_4$ and $HNO_3$ prepared at volume ratio of 30:10 and stirred for 12 h at 37° C. (room temperature). After completion of reaction (12 h), 400 mL water is added and its pH is adjusted to 7 with the help of $Na_2CO_3$ and NaOH. Reaction solution is left to slowly stir in ice bath for 3 h to remove the salts in the form of precipitation. After that, product is dialyzed using dialysis bag (molecular weight cut-off 2000 Da) for 2 days.

b. Preparation of Small Unilamellar Vesicles (Liposomes)

For liposome preparation, a suitable amount (100 mg) of L-alpha-dipalmitoylphosphatidylcholine, DPPC (phase transition temperature=41° C.), is dissolved in chloroform (6 mL). After complete removal of the chloroform (at 40° C. under reduced pressure), 10 mL of PBS (PBS, 150 mM, pH 7.4) is added to phospholipid film sample in order to obtain a 10 mg/mL lipid suspension in the form of large multilamellar vesicles during film hydration process. The suspension of multilamellar vesicles is then extruded above the transition temperature (41° C.) of the lipids using an extruder with polycarbonate membranes (mean size diameter: 400, 200 and finally 100 nm, Nucleopore).

c. Engineering of Biodegradable NIR Responsive Red Emissive Graphene Oxide Liposome Nano-Composite To Engineer a biodegradable nanocomposite, 100 mg of DPPC (phase transition temperature=41° C.), is dissolved in 6 mL chloroform. After complete removal of the chloroform (at 40° C. under reduced pressure), 10 mL of PBS containing 2 mg of fluorescent GOF (PBS, 150 mM, pH 7.4) is added to phospholipid film sample in order to obtain the large multilamellar vesicles during film hydration process. The suspension of multilamellar vesicles is then extruded above the transition temperature (41° C.) of the lipids using an extruder with polycarbonate membranes (mean size diameter: 400, 200 and finally 100 nm, Nucleopore). Further, above procedure is followed for drug loading experiment and 0.5 mg doxorubicin drug is used for filling hydrophilic cavity of liposome. The mass of drug loaded into nanocomposite is calculated by subtracting the mass of drug in the supernatant from the total mass of drug in initial solution. The amount of drug adsorbed is analyzed with UV-vis spectrophotometer.

d. Surface Decoration of Nanocomposite with Targeting Ligand

The functionalization of nanocomposite is carried out by two steps. In the first step, functional groups of GOF that are present on the external surface of the nanocomposite are activated by EDC/NHS agents and then cystamine is added in the reaction mixture. In the second step, folic acid (FA) is anchored on the amine functionalized nanocomposite. Folic acid (180 mg) is also activated by EDC (56 mg) and NHS (46 mg) in 16 ml of MPW for 12 h at room temperature. Further, the aqueous solution of amine functionalized nanocomposite (100 mg) is mixed with activated folic acid and allowed to react for 12 h. After completion of the reaction, the mixture is dialyzed using dialysis bag (molecular weight cut-off 2000 Da) for overnight.

e. Drug Release Study

For drug release study, 1.0 mL of DOX loaded nanocomposite is transferred into a dialysis bag (molecular weight cut-off 12 KD). The bag is subsequently placed in 100 mL of various buffer (pH 7.4, 4 with and without NIR laser) solutions and left to stir at 37° C. At different time intervals, 1 mL solution is collected and replaced with 1 mL of fresh PBS solution to keep volume constant. The amount of DOX in the release medium is measured by UV-Vis spectroscopy at the wavelength of 480 nm.

Example 3: In Vitro Studies a. Cell Culture

The normal L929 cells and MDA-MB-231 cancer cells are cultured in Dulbecco's Modified Eagle's Medium (DMEM Gibco, Carlsbad, Calif., USA) supplemented with 10% Fetal Bovine serum and penicillin/streptomycin, under 5% $CO_2$ atmosphere at 37° C.

b. In Vitro Cytotoxicity Assay

In vitro cytotoxicity studies are performed over L929 cells using 24 h MTT assay. Cells are seeded at density of $2 \times 10^4$ cells per well of 96-well plate. After overnight incubation at 5% $CO_2$ and 37° C., 100 μl of different concentrations (25-2000 μg/mL) of GOF, Lipo, GOF-Lipo, and GOF-Lipo-FA nanoparticles dispersed in media are added into the wells. After 24 h incubation wells are washed off with PBS and 20 μl of MTT dye is added. Formazan crystals formed after 4 h are dissolved by 200 μL of DMSO. Optical absorbance is recorded at 570 nm and 690 nm using microplate reader (Tecan Infinite 200 PRO). Percentage cell viability is calculated in reference to untreated cells (negative control).

c. Cellular Uptake

To check the cell targeting performance, folic acid (FA) is used as a targeting ligand and breast cancer cells MDA-MB-231 are treated with folic acid functionalized nanocomposite. Prior to this study the cancer cells seeded in 96 well plate at density of $2 \times 10^4$ cells/well and incubated overnight in incubator maintained at 5% $CO_2$ and 37° C. Then, wells are washed off with PBS and 100 μl of 200 μg/mL of GOF-Lipo-FA is added. After 5 h, wells are washed off with PBS twice to remove unbound nanocomposite. Thereafter, 4% paraformaldehyde solution is added to the cells and nuclei are stained with 4, 6-diamidino-2-phenylindole (DAPI). Cover slip is then mounted over a drop of 70% glycerol on glass slide to fix the phase of the cell. Images are captured using fluorescence microscope (Axio Observer Z1, Carl Zeiss). To evaluate the red fluorescence and Intracellular localization of nanocomposite, MDA-MB-231 cells are treated further for 24 h using same concentration of folic acid functionalized nanocomposite.

d. In Vitro Targeted Chemo, Photothermal and Combined Chemo-Photothermal Cancer Therapy An optical fibre coupled 808 nm NIR laser (1 W power) is used for this therapeutic experiment. Breast cancer cells MDA-MB-231 are treated with folic acid functionalized nanocomposite. Before this study the cancer cells seeded in 96 well plates at density of $2 \times 10^4$ cells/well and incubated overnight in incubator maintained at 5% $CO_2$ and 37° C. Then, cells are treated with 100 μl of (200 μg/ml.) GOF-Lipo, GOF-Lipo-FA and DOX-GOF-Lipo-FA with and without NIR exposure for 5 min. After 24 h incubation wells are washed off with PBS and 20 μl of MTT dye is added. Formazan crystals formed after 4 h are dissolved by 200 μL of DMSO. Optical absorbance is recorded at 570 nm and 690 nm using microplate reader (Tecan Infinite 200 PRO).

ADVANTAGES OF THE INVENTION

1. The nano-theranostic biodegradable composite is novel and never reported earlier.
2. It is collapses on therapy and biodegradable.
3. It is easily synthesized at ambient conditions even at large scale.
4. It emits NIR fluorescence for easy diagnosis via deep tissue penetration.
5. It absorbs NIR (600-900 nm) for localized photothermal therapy.
6. It has large hydrophilic cavity for high cargo.
7. It uses red fluorescent graphene oxide flakes (GOF) whose synthesis is rapid, one pot and at ambient conditions and is reported for the first time.
8. It exhibits hyperthermia (crossing 43° C.) within 2 min exposure of 808 nm NIR laser source with low power density (1 W/cm$^2$). This is superior compared to the counterparts available.
9. It is highly biocompatible (cell viability is more than 95%), efficiently targets the cancer cell and performs targeted combined chemo-photothermal therapy.

We claim:

1. A biodegradable nano composite comprising graphene oxide and a lipid in a liposome in a ratio of 0.005 to 0.03 by weight, characterized in that the graphene oxide is coated as a film on an inner side and an outer side of the liposome, wherein said nano composite is functionalized.

2. The nano composite as claimed in claim 1, wherein said nano composite is fluorescent and absorbs in the near-infrared region.

3. A composition comprising the nano composite as claimed in claim 1, along with a cargo selected from the group consisting of a drug, a biomolecule and a dye.

4. The composition as claimed in claim 3, wherein the drug in the cargo is Doxorubicin and the biomolecule is Deoxyribonucleic acid or Ribonucleic acid.

5. A process for the synthesis of the nano composite as claimed in claim 1, wherein said process comprises the steps of:
   a) dissolving the lipid in a volatile solvent to obtain a mixture;
   b) removing of the volatile solvent from the mixture obtained in step (a), followed by adding phosphate-buffered saline containing fluorescent graphene oxide nanoflakes in an amount in the range of 0.5 to 3 mg, to obtain a lipid suspension in the form of multilamellar vesicles during film hydration process; and
   c) extruding the suspension of multilamellar vesicles as obtained in step (b) at a transition temperature in the range of 40 to 50° C. of the lipid using an extruder with polycarbonate membranes to form said biodegradable nano composite.

6. The process as claimed in claim 5, wherein said lipid is selected from the group consisting of L-alpha-dipalmitoylphosphatidylcholine, 1,2-Dimyristoyl-sn-glycero-3-phosphorylcholine and 1,2-Dimyristoyl-sn-glycero-3-phosphorylglycerol sodium salt.

7. The process as claimed in claim 5, wherein said volatile solvent of step a) is selected from the group consisting of chloroform, and alcohol or mixtures thereof.

8. The process as claimed in claim 5, wherein said graphene oxide nanoflakes are synthesized by a process comprising the steps of:
   i) adding graphene oxide into a concentrated solution of sulfuric acid and nitric acid at volume ratio of 3.3 to 2.8 followed by stirring for a time period in the range of 12 to 14 h at a temperature in the range of 35 to 40° C. to afford a product; and
   ii) dialyzing the product of step i) at the temperature in the range of 35-40° C. by a dialysis bag having a molecular weight cut-off of 2000 Da for a period in the range of 2 to 4 days to afford the graphene oxide nanoflakes with specific emissions in the range of 600 to 850 nm.

9. A process for functionalization of the nano composite as claimed in claim 1 with a targeting ligand comprising the steps of:
   a) activating functional group of graphene oxide nanoflakes present on an external surface of the nano composite by 1-Ethyl-3-(3-dimethylaminopropyl) carbodiimide/N-Hydroxysuccinimide agent followed by adding cystamine in a reaction mixture to obtain an amine functionalized nanocomposite;
   b) anchoring folic acid on the amine functionalized nanocomposite;
   c) mixing an aqueous solution of the amine functionalized nano composite with activated folic acid and reacting for 12 hours; and
   d) dialyzing the mixture of step c) using a dialysis bag having a molecular weight cut-off of 2000 Da for a period in the range of 6 to 48 hours to obtain functionalized nano composite.

10. The process as claimed in claim 9, wherein said process is carried out at a temperature in the range of 37° C. to 40° C.

* * * * *